US007169194B2

(12) United States Patent
Lagrange

(10) Patent No.: US 7,169,194 B2
(45) Date of Patent: *Jan. 30, 2007

(54) DYE COMPOSITION COMPRISING AT LEAST ONE PARTICULAR TRICATIONIC DIRECT DYE, DYEING PROCESS, USE AND MULTI-COMPARTMENT DEVICES

(75) Inventor: Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 197 days.

This patent is subject to a terminal disclaimer.

(21) Appl. No.: 10/742,801

(22) Filed: Dec. 23, 2003

(65) Prior Publication Data

US 2004/0187227 A1    Sep. 30, 2004

Related U.S. Application Data

(60) Provisional application No. 60/468,735, filed on May 8, 2003.

(30) Foreign Application Priority Data

Dec. 23, 2002    (FR) .................................. 02 16565

(51) Int. Cl.
*A61K 7/13*    (2006.01)
(52) U.S. Cl. ...................... 8/405; 8/406; 8/407; 8/410; 8/411; 8/423; 8/426; 8/437; 8/562; 8/565; 8/566; 8/568; 8/570; 8/571; 8/572; 8/573; 8/574; 8/575; 8/576; 8/579; 549/200; 546/146; 552/100; 540/122
(58) Field of Classification Search ................ 8/405, 8/406, 407, 410, 411, 423, 426, 437, 562, 8/565, 566, 568, 570, 571, 572, 573, 574, 8/575, 576, 579; 549/200; 546/146; 552/100; 540/122
See application file for complete search history.

(56) References Cited

U.S. PATENT DOCUMENTS

| 2,528,378 A | 10/1950 | Mannheimer ............ 260/909.6 |
| 2,781,354 A | 2/1957 | Mannheimer ............ 260/309.6 |
| 2,798,053 A | 7/1957 | Brown ........................ 260/2.2 |
| 2,923,692 A | 2/1960 | Ackerman et al. ........ 260/117.6 |
| 3,578,387 A | 5/1971 | Zviak et al. .................. 8/10.1 |
| 3,915,921 A | 10/1975 | Schlatzer ................. 260/17.11 |
| RE30,199 E | 1/1980 | Rose et al. ..................... 8/10.2 |
| 4,237,243 A | 12/1980 | Quack et al. ................. 525/154 |
| 4,509,949 A | 4/1985 | Huang et al. ................. 586/558 |
| 4,557,732 A * | 12/1985 | Hahnke et al. ................. 8/538 |
| 4,670,546 A | 6/1987 | Dore et al. .................. 534/612 |
| 4,823,985 A | 4/1989 | Grollier et al. .................. 222/1 |
| 5,061,289 A | 10/1991 | Clausen et al. ................. 8/405 |
| 5,380,340 A | 1/1995 | Neunhoeffer et al. ........... 8/409 |
| 5,534,267 A | 7/1996 | Neunhoeffer et al. ....... 424/701 |
| 5,663,366 A | 9/1997 | Neunhoeffer et al. .... 548/371.4 |
| 5,708,151 A | 1/1998 | Möckli ....................... 534/608 |
| 5,766,576 A | 6/1998 | Löwe et al. ................... 424/62 |
| 5,980,587 A | 11/1999 | Samain ............................ 8/426 |
| 6,099,592 A | 8/2000 | Vidal et al. ..................... 8/409 |
| 6,099,593 A | 8/2000 | Terranova et al. ............. 8/409 |
| 6,284,003 B1 | 9/2001 | Rose et al. ..................... 8/412 |
| 6,338,741 B1 | 1/2002 | Vidal et al. ..................... 8/409 |
| 6,368,360 B2 | 4/2002 | Samain ............................ 8/426 |
| 6,645,258 B2 | 11/2003 | Vidal et al. ..................... 8/405 |
| 2001/0001333 A1 | 5/2001 | Samain ............................ 8/426 |
| 2002/0050013 A1 | 5/2002 | Vidal et al. ..................... 8/405 |
| 2003/0019051 A9 | 1/2003 | Vidal et al. ..................... 8/405 |

FOREIGN PATENT DOCUMENTS

| DE | 23 59 399 A1 | 6/1975 |
| DE | 33 13 965 | 10/1983 |
| DE | 38 43 892 A1 | 6/1990 |
| DE | 41 33 957 A1 | 4/1993 |
| DE | 195 43 988 A1 | 5/1997 |
| EP | 0 216 479 B1 | 1/1987 |
| EP | 0 714 954 B1 | 6/1996 |
| EP | 0 770 375 A1 | 5/1997 |
| FR | 1 584 965 | 1/1970 |
| FR | 2 416 723 A1 | 9/1979 |
| FR | 2 586 913 A1 | 3/1987 |
| FR | 2 733 749 A1 | 11/1996 |

(Continued)

OTHER PUBLICATIONS

Toyoki Kunitake et al., "DSC Studies of the Phase Transition Behavior of Synthetic Bilayer Membranes Part II Bilayer Membranes of Single-Chain and Triple-Chain Amphiphiles," Memoirs of the Faculty of Engineering, Kyushu University, vol. 46, No. 2, Jun. 1986, pp. 245-263.

(Continued)

*Primary Examiner*—Eisa Elhilo
(74) *Attorney, Agent, or Firm*—Finnegan, Henderson, Farabow, Garrett & Dunner LLP

(57) ABSTRACT

A dye composition for dyeing human keratin fibers, such as hair, comprising at least one direct tricationic dye of formula (I) below:

$$\text{Col—Z—Col} \qquad (I)$$

wherein:

Col, which may be identical or different, is a monocationic dye chosen from azo dyes, cyanomethine dyes and phenothiazine dyes and Z is chosen from linear and branched, saturated and unsaturated $C_1$–$C_{20}$ hydrocarbon-based groups comprising at least one nitrogen atom and bearing a cationic charge. Also processes for dyeing human keratin fibers using the dye composition, to the use of the at least one direct tricationic dye of formula (I) as direct dyes, and to multi-compartment devices.

32 Claims, No Drawings

FOREIGN PATENT DOCUMENTS

| | | |
|---|---|---|
| FR | 2 741 798 A1 | 6/1997 |
| FR | 2 750 048 A1 | 12/1997 |
| FR | 2 825 702 | 12/2002 |
| GB | 1 026 978 | 4/1966 |
| GB | 1 153 196 | 5/1969 |
| JP | 53-95693 | 8/1978 |
| JP | 55-22638 | 2/1980 |
| JP | 88-169571 | 7/1988 |
| JP | 2-19576 A1 | 1/1990 |
| JP | 5-163124 | 6/1993 |
| JP | 6-271435 | 9/1994 |
| JP | 2526099 B2 | 11/1996 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 01/66646 A1 | 9/2001 |

OTHER PUBLICATIONS

English language Derwent Abstract of FR 2 825 702, Dec. 13, 2003.

Kirk-Othmer, "Enclyopedia of Chemical Technology", "Biopolymers", 3$^{rd}$ Edition, vol. 3, pp. 896-900, 1978.

Kirk-Othmer, "Enclyopedia of Chemical Technology", "Microbial Polysaccharides", 3$^{rd}$ Edition, vol. 15, pp. 439-458 (1981).

MacGregor, et al., "Polymers in Nature", Chapter 6, pp. 240-328, (1980).

Porter, M.R., Handbook of Surfactants, Chapter 7, pp. 116-178, (1991).

English language Derwent Abstract of non-English language document No. EP 0 770 375.

English language Derwent Abstract of non-English language document No. JP 5-163124.

English language JAPIO Abstract of non-English language document No. JP 53-095693.

English language Derwent Abstract of non-English language document No. JP 55-22638.

English language Derwent Abstract of non-English language document No. JP 6-271435.

English language Derwent Abstract of non-English language document No. JP 2-19576 and JP 2526099.

French Search Report for FR 0216565 (French Priority Application for U.S. Appl. No. 10/742,801) the present application, Examiner M. Pregetter, Sep. 15, 2003.

* cited by examiner

DYE COMPOSITION COMPRISING AT LEAST ONE PARTICULAR TRICATIONIC DIRECT DYE, DYEING PROCESS, USE AND MULTI-COMPARTMENT DEVICES

This application claims benefit of U.S. Provisional Application No. 60/468,735, filed May 8, 2003.

Disclosed herein are dye compositions for dyeing human keratin fibres, such as hair, comprising at least one direct tricationic dye, and to processes for dyeing human keratin fibres using such a composition.

It is well-known practice to dye human keratin fibres, such as hair, with dye compositions comprising oxidation dye precursors, generally known as oxidation bases. The oxidation bases are colorless or weakly colored compounds, that, when combined with oxidizing products, may give rise to colored compounds by a process of oxidative condensation.

It is also well-known that the shades obtained with these oxidation bases may be varied by combining them with couplers or coloration modifiers. The variety of molecules used as oxidation bases and couplers may make it possible to obtain a wide range of colors.

The oxidation dyeing process comprises applying to keratin fibres at least one oxidation base and/or a mixture of oxidation bases and couplers with an oxidizing agent, for example aqueous hydrogen peroxide solution, leaving the agents on the fibres and then rinsing the fibres. The colorations resulting therefrom may be permanent, strong and resistant to external agents, such as, light, bad weather, washing, perspiration and rubbing. This process, which may be applied at basic pH, may make it possible simultaneously to dye and lighten the fibres, which is reflected in practice by the possibility of obtaining a final coloration that is lighter than the original fibre color. In addition, lightening of the fibres may have the advantageous effect of generating a unified color in the case of grey hair, and may bring out the colour, i.e. make it more visible, in the case of naturally pigmented hair.

It is also well-known practice to dye human keratin fibres with a direct dye. The process conventionally used in direct dyeing comprises applying to the keratin fibres direct dyes, which are coloured and colouring molecules that have affinity for the fibres, leaving the dyes on the fibres and then rinsing the fibres.

It is well-known practice, for example, to use nitrobenzene, anthraquinone, nitropyridine, azo, xanthene, acridine, azine or triarylmethane direct dyes.

The colorations resulting therefrom may be chromatic colorations, but also may be merely temporary or semi-permanent because of the nature of the interactions linking the direct dyes to the keratin fibres. Desorption from the surface and/or core of the fibres may be responsible for the poor dyeing power and the poor fastness of these direct dyes with respect to washing or perspiration. These direct dyes may also be light-sensitive due to the poor resistance of the chromophore to photochemical attack, which may lead over time to fading of the coloration of the hair. In addition, the light-sensitivity of these direct dyes is dependent on their uniform distribution or their distribution as aggregates in the keratin fibres.

Further, it is also well-known practice to use direct dyes in combination with oxidizing agents. However, the direct dyes may be sensitive to the action of oxidizing agents such as aqueous hydrogen peroxide solution, and reducing agents such as sodium bisulphite, which may make them difficult to use in lightening direct dyeing compositions based on aqueous hydrogen peroxide solution and based on a basifying agent, and or in oxidation dye compositions in combination with precursors such as oxidation bases or couplers.

For example, it has been proposed in Patent Application Nos. FR-1 584 965 and JP-062 711 435 to dye hair with dye compositions based on nitro direct dyes and/or dispersed azo dyes and an ammoniacal aqueous hydrogen peroxide solution, by applying to the hair a mixture of the dyes and the oxidizing agent, prepared just before use. However, the colorations obtained may be insufficiently fast, and may disappear on shampooing, thus allowing the lightening of the hair fibres to show through. Such a coloration may become unattractive by changing over time.

It has also been proposed in Patent Application Nos. JP-53 95693 and JP-55 022638 to dye hair with compositions based on cationic oxazine direct dyes and ammoniacal aqueous hydrogen peroxide solution, by applying to the hair an ammoniacal aqueous hydrogen peroxide solution in a first step, and then a composition based on the oxazine direct dye in a second step. This coloration may be unsatisfactory, due to the fact that it requires a process that may be made too slow by the leave-in times of the two successive steps. If, moreover, an extemporaneous mixture of the oxazine direct dye with ammoniacal aqueous hydrogen peroxide solution is applied to the hair, either no coloration is obtained, or, a virtually non-existent coloration of the hair fibres may be obtained.

More recently, Patent Application No. FR 2 741 798 has described dye compositions comprising direct dyes comprising at least one quaternized nitrogen atom of the azo or azomethine type, wherein the compositions are for extemporaneous mixing at basic pH with an oxidizing composition. These compositions may make it possible to obtain colorations with uniform, fast and shiny glints. However, they may not allow keratin fibres to be dyed as strongly as with oxidation dye compositions.

There is thus a desire to find chromatic direct dyes that allow human keratin fibres to be dyed as strongly as oxidation dyes, which may also be as light-fast as the latter dyes, and which may be resistant to bad weather, washing and perspiration. There is a desire for chromatic direct dyes that may be sufficiently stable in the presence of oxidizing and reducing agents to be able to simultaneously obtain lightening of the fibres either by using lightening direct compositions comprising them, or by using oxidation dye compositions based on oxidation dye precursors comprising them. There is also a desire to find direct dyes that may produce rises in color comparable to those obtained with oxidation dye precursors.

In addition, the present inventor has sought to obtain dyes that show one or more of the following characteristics: good harmlessness, little or no degradation of the keratin fibres and less selectivity compared with standard dyes.

At least one of these aims may be achieved with the compositions disclosed herein. Accordingly, disclosed herein are compositions for dyeing human keratin fibres, such as hair, comprising at least one direct tricationic dye of formula (I) below:

Col—Z—Col      (I)

wherein:

Col, which may be identical or different, is a monocationic dye chosen from azo dyes, methine dyes, azomethine dyes, phenothiazine dyes, triarylmethane dyes, xanthene dyes, phenanthridine dyes and phthalocyanin dyes and Z is chosen from linear and branched, saturated and unsaturated $C_1$–$C_{20}$ hydrocarbon-based groups comprising at least one nitrogen atom and bearing a cationic charge.

As used herein:

the term "azo dye" means a molecule or a molecule residue
    that absorbs light radiation in the visible region ranging from 400 nm to 750 nm and comprises in its structure at least one sequence (A) not included in a ring;

 (A)

the term "methine dye" means a molecule or a molecule residue that absorbs light radiation in the visible region ranging from 400 nm to 750 nm and comprises in its structure at least one sequence (B) not included in a ring;

 (B)

the term "azomethine dye" means a molecule or a molecule residue that absorbs light radiation in the visible region ranging from 400 nm to 750 nm

 (C)

and comprises in its structure at least one sequence (C) not included in a ring;

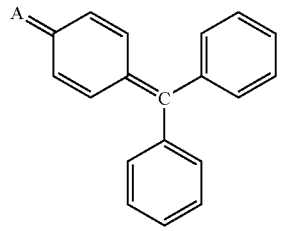 (D)

the term "triarylmethane dye" means a molecule or a molecule residue that absorbs light radiation in the visible region ranging from 400 nm to 750 nm and comprises in its structure at least one sequence (D), wherein A is chosen from an oxygen atom and a nitrogen atom;

the term "xanthene dye" means a molecule or a molecule residue that absorbs light radiation in the visible region ranging from 400 nm to 750 nm and comprises in its structure at least one sequence (E);

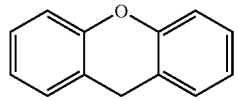 (E)

the term "phenanthridine dye" means a molecule or a molecule residue that absorbs light radiation in the visible region ranging from 400 nm to 750 nm and comprises in its structure at least one sequence (F);

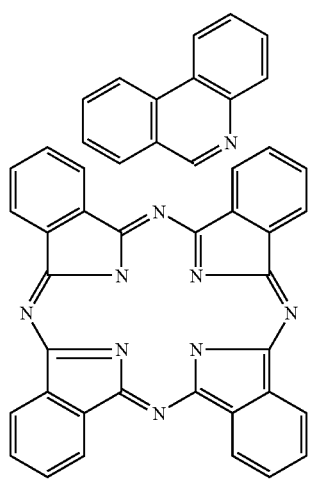 (F)

the term "phthalocyanin dye" means a molecule or a molecule residue that absorbs light radiation in the visible region ranging from 400 to 750 nm and comprises in its structure at least one sequence (G); and

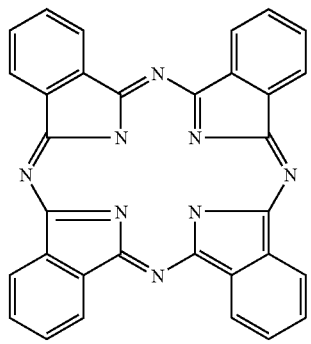

the term "phenothiazine dye" means a molecule or a molecule residue that absorbs light radiation in the visible region ranging from 400 to 750 nm and comprises in its structure at least one sequence (H).

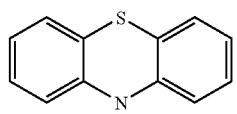 (H)

As used for formula (I), the term "cationic charge" means any quaternized nitrogen atom.

As used herein, the term "$C_1$–$C_{20}$ hydrocarbon-based group" means a $C_1$–$C_{20}$ aliphatic chain, such as a $C_6$–$C_{18}$ aliphatic chain which may be interrupted with at least one (ranging from 1 to 5) hetero atoms, for example, chosen from nitrogen, oxygen, sulphur and phosphorus, this chain possibly comprising at least one entity chosen from (from 1 to 5) aromatic rings, (from 1 to 5) aromatic and saturated heterocycles, (from 1 to 5) aliphatic rings, or possibly being substituted with at least one (from 1 to 5) group chosen from hydroxyl, carboxyl, ($C_1$–$C_4$)alkoxycarbonyl, hydrogenocarbonyl, $C_1$–$C_4$ alkoxy, $C_2$–$C_4$ acyl, amino, mono- and dialkylamino, mono- and di($C_1$–$C_4$ hydroxyalkyl)amino, cyano, nitro and sulphonato groups.

The aliphatic chain may, for example, comprise at least one bond chosen from double bonds and triple bonds. This chain may also comprise at least one aromatic group such as a benzene or naphthalene ring. The chain may also form at least one ring chosen from 3- to 6-membered carbon-based rings.

The attachment of the two identical dye radicals Col to the group Z may be performed directly on the cationic nitrogen-based groups of the dyes, on at least one other atom of the dye molecule, or via at least one linking arm.

Z may be a group of formula (II):

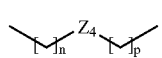 (II)

wherein n is an integer, for example, ranging from 1 to 10 and, further, for example, from 2 to 5;

p is an integer ranging, for example, from 1 to 10 and, further, for example, ranging from 2 to 5; and $Z_4$ is chosen from a radical $^{\oplus}NR_1R_2$, wherein $R_1$ and $R_2$, which may be identical or different, are each chosen from $C_1$–$C_6$ alkyl radicals; and a 5- to 8-membered monocationic heterocycle, which may or may not be fused to a benzene nucleus and which is optionally substituted with at least one entity chosen from halogen atoms and $C_1$–$C_4$ alkyl, hydroxyl and amino radicals.

In one embodiment, $Z_4$ is a $^{\oplus}NR_1R_2$ radical.

In another embodiment, the Col radical is chosen from at least one of triarylmethane dyes, azo dyes, and azomethine dyes.

The at least one direct tricationic dye of formula (I) are compounds that are known per se. For example, the at least one direct tricationic dye of formula (I) may be chosen from the following:

1-Hexadecanaminium 16,16'-[(dimethylimino)bis(16,1-hexadecanediyloxy-4,1-phenylenemethylidynenitrilo-4,1-phenyleneoxy)]bis[N,N,N-trimethyl tribromide;

1-Decanaminium 10,10'-[(dimethylimino)bis(10,1-decanediyloxy-4,1-phenylenemethylidynenitrilo-4,1-phenyleneoxy)]bis[N,N,N-trimethyl tribromide;

bis[2-({4-[(4-Dimethylaminophenyl)(cyclohexa-2,5-dienylidene}-4-dimethylammonium)methylene]phenyl}ethylamino)ethyl]dimethyl ammonium;

bis[2-({4-[(4-Dimethylaminophenyl)(cyclohexa-2,5-dienylidene}-4-dimethylammonium)methylene]phenyl}ethylamino)ethyl]ethylmethyl ammonium; and Benzothiazolium 2,2'-[(methylpropylimino)bis-[(2-hydroxytrimethylene)(ethylimino)-p-phenyleneazo]]bis[6-ethoxy-3-methyl trichloride, diacetate ester.

The at least one direct tricationic direct dye of formula (I) may be present in an amount ranging from approximately 0.001% to approximately 5% by weight, further, for example, from approximately 0.05% to approximately 2% by weight, relative to the total weight of the dye composition.

The compositions disclosed here may further comprise at least one cosmetic adjuvant chosen from monoalcohols such as alkanols; polyols; anionic, cationic, nonionic, amphoteric and zwitterionic surfactants; and mineral and organic thickeners, for example, anionic, cationic, nonionic and amphoteric associative polymers.

The thickeners may, for example, be chosen from:
(i) associative thickeners;
(ii) crosslinked acrylic acid homopolymers;
(iii) crosslinked copolymers of (meth)acrylic acid and of $(C_1$–$C_6)$alkyl acrylate;
(iv) nonionic homopolymers and copolymers comprising ethylenically unsaturated monomeric units of ester and/or amide;
(v) ammonium acrylate homopolymers and copolymers of ammonium acrylate and of acrylamide;
(vi) polysaccharides; and
(vii) $C_{12}$–$C_{30}$ fatty alcohols.

As used herein, the expression "associative thickener" means an amphiphilic thickener comprising both hydrophilic units and hydrophobic units, for example, comprising at least one $C_8$–$C_{30}$ fatty chain and at least one hydrophilic unit.

The associative thickeners that may be used in the compositions disclosed herein may, for example, be chosen from:
(i) nonionic amphiphilic polymers comprising at least one fatty chain and at least one hydrophilic unit;
(ii) anionic amphiphilic polymers comprising at least one hydrophilic unit and at least one fatty-chain unit;
(iii) cationic amphiphilic polymers comprising at least one hydrophilic unit and at least one fatty-chain unit; and
(iv) amphoteric amphiphilic polymers comprising at least one hydrophilic unit and at least one fatty-chain unit;
wherein the fatty chains of the above-mentioned polymers comprise from 10 to 30 carbon atoms.

The nonionic amphiphilic polymers comprising at least one fatty chain and at least one hydrophilic unit may, for example, be chosen from:
(1) celluloses modified with groups comprising at least one fatty chain; examples of these celluloses include:
  hydroxyethylcelluloses modified with at least one group comprising at least one fatty chain, such as, at least one group chosen from alkyl, arylalkyl and alkylaryl groups, wherein the alkyl groups may, for example, be $C_8$–$C_{22}$ alkyl groups, such as the product NATROSOL Plus Grade 330 CS ($C_{16}$ alkyls) sold by the company Aqualon, and the product BERMOCOLL EHM 100 sold by the company Berol Nobel; and
  celluloses modified with at least one polyalkylene glycol alkylphenyl ether group, such as the product AMERCELL Polymer HM-1500 (polyethylene glycol (15) nonylphenyl ether) sold by the company Amerchol;
(2) hydroxypropyl guars modified with at least one group comprising at least one fatty chain, such as the product ESAFLOR HM 22 ($C_{22}$ alkyl chain) sold by the company Lamberti, and the products MIRACARE XC95-3 ($C_{14}$ alkyl chain) and RE205-1 ($C_{20}$ alkyl chain) sold by the company Rhodia Chimie;
(3) polyether urethanes comprising at least one fatty chain, such as $C_{10}$–$C_{30}$ alkyl and alkenyl groups, for example, the products DAPRAL T 210 and DAPRAL T 212 sold by the company Akzo and the products ACULYN 44 and ACULYN 46 sold by the company Rohm & Haas;
(4) copolymers of vinylpyrrolidone and of hydrophobic fatty-chain monomers; examples of these copolymers include:
  the products ANTARON V216 and GANEX V216 (vinylpyrrolidone/hexadecene copolymer) sold by the company I.S.P.,
  the products ANTARON V220 and GANEX V220 (vinylpyrrolidone/eicosene copolymer) sold by the company I.S.P.;
(5) copolymers of $C_1$–$C_6$ alkyl acrylates or methacrylates and of amphiphilic monomers comprising at least one fatty chain, such as, the oxyethylenated methyl methacrylate/stearyl acrylate copolymer sold by the company Goldschmidt under the name ANTIL 208; and
(6) copolymers of hydrophilic acrylates or methacrylates and of hydrophobic monomers comprising at least one fatty chain, such as, for example, the polyethylene glycol methacrylate/lauryl methacrylate copolymer.

The anionic amphiphilic polymers comprising at least one hydrophilic unit and at least one fatty-chain unit may, for example, be chosen from those polymers comprising at least one fatty-chain allyl ether unit and at least one hydrophilic unit comprising at least one ethylenic unsaturated anionic monomeric unit, for example, a vinylcarboxylic acid and, further, for example, an acrylic acid and a methacrylic acid, wherein the at least one fatty-chain allyl ether unit is chosen from monomers of formula (V) below:

$$CH_2=C(R1)CH_2OB_nR \qquad (V)$$

wherein R1 is chosen from H and $CH_3$; B is a ethyleneoxy radical; n is zero or is an integer ranging from 1 to 100; and R is a hydrocarbon-based radical chosen from alkyl, arylalkyl, aryl, alkylaryl and cycloalkyl radicals, comprising, for example, from 10 to 30 carbon atoms, further, for example, from 10 to 24 carbon atoms and even, further, for example, from 12 to 18 carbon atoms.

For example, the unit of formula (V) can be a unit wherein R1 is a H atom, n is equal to 10 and R is a stearyl ($C_{18}$) radical.

The anionic amphiphilic polymers of this type are described and prepared, according to an emulsion polymerization process, in Patent No. EP-0 216 479 B2.

These anionic amphiphilic polymers may, for example, be chosen from polymers formed from 20% to 60% by weight of acrylic acid and/or of methacrylic acid, from 5% to 60% by weight of lower alkyl(meth)acrylates, from 2% to 50% by weight of the at least one fatty-chain allyl ether of formula (V), and from 0% to 1% by weight of a crosslinking agent which comprises at least onewell-known copolymerizable unsaturated polyethylenic monomers, such as diallyl phthalate, allyl(meth)acrylate, divinylbenzene, (poly)ethylene glycol dimethacrylate or methylenebisacrylamide.

Further, for example, the anionic amphiphilic polymers may be chosen from crosslinked terpolymers of methacrylic acid, of ethyl acrylate and of polyethylene glycol (10 EO) stearyl ether (Steareth-10), for example, those polymers sold by the company Ciba under the names SALCARE SC 80 and SALCARE SC 90, which are aqueous 30% emulsions of a crosslinked terpolymer of methacrylic acid, of ethyl acrylate and of steareth-10 allyl ether (40/50/10).

The anionic amphiphilic polymers can also be chosen from polymers comprising at least one hydrophilic unit of unsaturated olefinic carboxylic acid, and at least one hydrophobic unit such as a hydrophobic unit comprising a ($C_{10}$–$C_{30}$) alkyl ester of an unsaturated carboxylic acid, which may be used in the compositions disclosed herein, for example, polymers chosen from polymers wherein the at least one hydrophilic unit of unsaturated olefinic carboxylic acid is chosen from monomers of formula (VI) below:

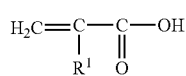

(VI)

wherein $R^1$ is chosen from H, $CH_3$, and $C_2H_5$, such as, acrylic acid, methacrylic acid and ethacrylic acid units, wherein the at least one hydrophobic unit such as a hydrophobic unit comprising a ($C_{10}$–$C_{30}$) alkyl ester of an unsaturated carboxylic acid is chosen from monomers of formula (VII) below:

$$H_2C=CR^1-CO-OR^2 \quad (VII)$$

wherein $R^1$ is chosen from H, $CH_3$, and $C_2H_5$ (such as acrylate, methacrylate and ethacrylate units) and, for example, H (acrylate units) and $CH_3$ (methacrylate units) and $R^2$ is chosen from $C_{10}$–$C_{30}$ alkyl radicals, such as $C_{12}$–$C_{22}$ alkyl radicals.

The ($C_{10}$–$C_{30}$)alkyl esters of unsaturated carboxylic acids may comprise, for example, lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate and dodecyl methacrylate.

The anionic amphiphilic polymers of this type are disclosed and prepared, for example, according to U.S. Pat. Nos. 3,915,921 and 4,509,949.

The anionic amphiphilic polymers that can be used in the compositions disclosed herein may further be chosen from polymers formed from a mixture of monomers. The anionic amphilphilic polymers comprising monomers chosen from at least one of:

(i) acrylic acid, an ester of formula (VIII) below:

$$H_2C=CR^1-CO-OR^2 \quad (VIII)$$

wherein $R^1$ is chosen from H and $CH_3$, $R^2$ is chosen from alkyl radicals comprising from 12 to 22 carbon atoms, and a crosslinking agent, examples of such polymers include, polymers comprising from 60% to 95% by weight of acrylic acid (hydrophilic unit), 4% to 40% by weight of $C_{10}$–$C_{30}$ alkyl acrylate (hydrophobic unit), and 0% to 6% by weight of crosslinking polymerizable monomer, or 96% to 98% by weight of acrylic acid (hydrophilic unit), 1% to 4% by weight of $C_{10}$–$C_{30}$ alkyl acrylate (hydrophobic unit) and 0.1% to 0.6% by weight of crosslinking polymerizable monomer, and (ii) acrylic acid and lauryl methacrylate, such as the product formed from 66% by weight of acrylic acid and 34% by weight of lauryl methacrylate.

The crosslinking agent is a monomer comprising at least one group

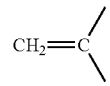

with at least one other polymerizable group whose unsaturated bonds are not conjugated. For example, the crosslinking agent may be chosen from polyallyl ethers such as, polyallylsucrose and polyallylpentaerythritol.

Among the polymers above, examples include the products sold by the company Goodrich under the trade names PEMULEN TR1, PEMULEN TR2, CARBOPOL 1382, and, further, for example, PEMULEN TR1, and the product sold by the company S.E.P.C. under the name Coatex SX.

The anionic amphiphilic fatty-chain polymers comprising at least one hydrophilic unit and at least one fatty chain, may be an ethoxylated copolymer of methacrylic acid/methyl acrylate/alkyl dimethyl-meta-isopropenylbenzylisocyanate sold under the name VISCOPHOBE DB 1000 by the company Amerchol.

The cationic amphiphilic polymers used in the compositions disclosed herein may, for example, be chosen from quaternized cellulose derivatives and polyacrylates comprising amino side groups.

The quaternized cellulose derivatives may, for example, be chosen from
  quaternized celluloses modified with at least one group comprising at least one fatty chain, for example, at least one group chosen from alkyl, arylalkyl and alkylaryl groups comprising at least 8 carbon atoms and
  quaternized hydroxyethylcelluloses modified with at least one group comprising at least one fatty chain, for example, at least one group chosen from alkyl, arylalkyl and alkylaryl groups comprising at least 8 carbon atoms.

Quaternized or non-quaternized polyacrylates comprising amino side groups, and comprising, for example, hydrophobic groups, such as STEARETH 20 (polyoxyethylenated (20) stearyl alcohol) or ($C_{10}$–$C_{30}$)alkyl PEG-20 itaconate.

The alkyl radicals borne by the above quaternized celluloses or hydroxyethylcelluloses may, for example, comprise from 8 to 30 carbon atoms.

The aryl radicals may, for example, be chosen from phenyl, benzyl, naphthyl and anthryl groups.

Examples of quaternized alkylhydroxyethylcelluloses comprising at least one $C_8$–$C_{30}$ fatty chain which may be used in the compositions disclosed herein include the products QUATRISOFT LM 200, QUATRISOFT LM-X 529-18-A, QUATRISOFT LM-X 529-18B ($C_{12}$ alkyl) and QUATRISOFT LM-X 529-8 ($C_{18}$ alkyl) sold by the company Amerchol, and the products CRODACEL QM, CRODACEL QL ($C_{12}$ alkyl) and CRODACEL QS ($C_{18}$ alkyl) sold by the company Croda.

Examples of polyacrylates comprising amino side chains include the polymers 8781-124B or 9492-103 or Structure Plus from the company National Starch.

The amphoteric amphiphilic polymers comprising at least one hydrophilic unit and at least one fatty chain may, for example, be chosen from copolymers of methacrylamidopropyltrimethylammonium chloride/acrylic acid/$C_{10}$–$C_{30}$ alkyl methacrylate, wherein the alkyl radical may, for example, be a stearyl radical.

For example, the associative thickeners in the cosmetic compositions disclosed herein may have, in solution or in dispersion at a concentration of 1% active material in water, a viscosity, measured using a Rheomat RM 180 rheometer at 25° C., of greater than 0.1 ps and even further, for example, of greater than 0.2 cp, at a shear rate of 200 $s^{-1}$ (i) Examples of crosslinked acrylic acid homopolymers include homopolymers crosslinked with an allylic alcohol ether of the sugar series, such as, the products sold under the names CARBOPOL 980, 981, 954, 2984 and 5984 by the company Goodrich or the products sold under the names Synthalen M and Synthalen K by the company 3 VSA.

(ii) Examples of crosslinked copolymers of (meth)acrylic acid and of $C_1$–$C_6$ alkyl acrylate include the product sold under the name VISCOATEX 538C by the company Coatex, which is a crosslinked copolymer of methacrylic acid and of ethyl acrylate as an aqueous dispersion containing 38% active material, or the product sold under the name ACULYN 33 by the company Rohm & Haas, which is a crosslinked copolymer of acrylic acid and of ethyl acrylate as an aqueous dispersion containing 28% active material.

(iii) Examples of nonionic homopolymers or copolymers comprising ethylenically unsaturated monomeric units of ester and/or amide, include the products sold under the names: CYANAMER P250 by the company Cytec (polyacrylamide); PMMA MBX-8C by the company US Cosmetics (methyl methacrylate/ethylene glycol dimethacrylate copolymer); ACRYLOID B66 by the company Rohm & Haas (butyl methacrylate/methyl methacrylate copolymer); and BPA 500 by the company Kobo (polymethyl methacrylate).

(iv) A further example includes the ammonium acrylate homopolymers sold under the name MICROSAP PAS 5193 by the company Hoechst.

Examples of copolymers of ammonium acrylate and of acrylamide include the product sold under the name BOZEPOL C NOUVEAU or the product PAS 5193 sold by the company Hoechst (which are described and prepared in documents FR-2 416 723, U.S. Pat. No. 2,798,053 and U.S. Pat. No. 2,923,692).

(v) The thickening polysaccharides may, for example, be chosen from at least one of glucans, modified and unmodified starches (such as those derived, for example, from cereals, such as wheat, corn and rice, from vegetables, such as yellow pea, and tubers, such as potato and cassava), amylose, amylopectin, glycogen, dextrans, celluloses and derivatives thereof (methylcelluloses, hydroxyalkylcelluloses, ethylhydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans such as guar gums and nonionic derivatives thereof (hydroxypropyl guar) and xanthan gums.

For example, the compounds of this type that may be used in the compositions disclosed herein may be chosen from those described in "Encyclopedia of Chemical Technology", Kirk-Othmer, Third Edition, 1982, volume 3, pp. 896–900, and volume 15, pp. 439–458, in "Polymers in Nature" by E. A. MacGregor and C. T. Greenwood, published by John Wiley & Sons, Chapter 6, pp. 240–328, 1980, and in "Industrial Gums—Polysaccharides and their Derivatives", edited by Roy L. Whistler, Second Edition, published by Academic Press Inc., the content of these three publications being entirely included in the present patent application by way of reference.

Starches, guar gums and celluloses and derivatives thereof may, for example, be used in the compositions disclosed herein.

The guar gums may, for example, be chosen from modified and unmodified guar gums.

The unmodified guar gums may, for example, be chosen from the products sold under the name VIDOGUM GH 175 by the company Unipectine and under the names MEYPROGUAR 50 and JAGUAR C by the company Meyhall.

The modified nonionic guar gums may, for example, be chosen from guar gums modified with at least one group chosen from $C_1$–$C_6$ hydroxyalkyl groups.

For example, the hydroxyalkyl groups may be chosen from hydroxymethyl, hydroxyethyl, hydroxypropyl and hydroxybutyl groups. These guar gums are well known by those of ordinary skill in the art and can be prepared, for example, by reacting the corresponding alkene oxides such as, propylene oxides, with the guar gum so as to obtain a guar gum modified with, for example, at least one hydroxypropyl group.

The degree of hydroxyalkylation, which corresponds to the number of alkylene oxide molecules consumed by the number of free hydroxyl functions present on the guar gum, may, for example, range from 0.4 to 1.2.

These nonionic guar gums optionally modified with hydroxyalkyl groups are sold, for example, under the trade names JAGUAR HP8, JAGUAR HP60, JAGUAR HP120, JAGUAR DC 293 and JAGUAR HP 105 by the company Rhodia Chimie (Meyhall) or under the name GALACTASOL 4H4FD2 by the company Aqualon.

Examples of celluloses that can be used include hydroxyethylcelluloses and hydroxypropylcelluloses. For example, the products sold under the names KLUCEL EF, KLUCEL H, KLUCEL LHF, KLUCEL MF and KLUCEL G by the company Aqualon.

The fatty alcohols may, for example, be chosen from myristyl alcohol, cetyl alcohol, stearyl alcohol and behenyl alcohol.

The mineral thickeners may, for example, be chosen from clays.

The thickeners may be present, for example, in an amount ranging from approximately 0.001% to approximately 20% by weight, further, for example, from approximately 0.01% to approximately 10% by weight, and, even further, for example, from approximately 0.1% to approximately 3% by weight, relative to the total weight of the composition.

The compositions disclosed herein further comprise at least one surfactant, which may be present in an amount ranging from approximately 0.1% to approximately 60% by weight, further, for example, from approximately 3% to approximately 40% by weight, and even further, for example, from approximately 5% to approximately 30% by weight, relative to the total weight of the composition.

The at least one surfactant may be chosen from anionic, amphoteric, nonionic and cationic surfactants.

The at least one surfactant which is suitable for use in the composition disclosed herein may, for example, be chosen from the following:

(i) Anionic Surfactant(s):

Appropriate anionic surfactants would be readily apparent to the skilled artisan. The nature of the anionic surfactants do not assume a critical character within the context of the embodiments disclosed herein.

For example, the anionic surfactants which may be used in the compositions disclosed herein may be chosen from at least one of the following, non-limiting list, salts, for example, alkaline salts, such as, sodium salts; ammonium salts; amine salts; amino alcohol salts and magnesium salts of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates, wherein the alkyl and acyl radical of all of these various compounds, for example, comprise from 8 to 24 carbon atoms, and the aryl radical may, for example, be chosen from a phenyl group and a benzyl group.

The anionic surfactants may also, for example, be chosen from at least one fatty acid salts, such as the salts of oleic, ricinoleic, palmitic and stearic acids; coconut oil acid and hydrogenated coconut oil acid; and acyl lactylates wherein the acyl radical comprises from 8 to 20 carbon atoms. The anionic surfactants may also be chosen from at least one weakly anionic surfactants, such as alkyl-D-galactosiduronic acids and salts thereof, as well as polyoxyalkylenated ($C_6$–$C_{24}$) alkyl ether carboxylic acids, polyoxyalkylenated ($C_6$–$C_{24}$) alkylaryl ether carboxylic acids, polyoxyalkylenated ($C_6$–$C_{24}$) alkylamido ether carboxylic acids and salts thereof, for example, those comprising from 2 to 50 ethylene oxide groups.

The anionic surfactants may, for example, be chosen from at least one of alkyl sulphate salts and alkyl ether sulphate salts.

(ii) Nonionic Surfactant(s):

The nonionic surfactants are, themselves also, compounds that are well known per se (see, for example, in this respect "Handbook of Surfactants" by M. R. Porter, published by Blackie & Son (Glasgow and London), 1991, pp. 116–178). Appropriate non-ionic surfactants will be readily apparent to the skilled artisan. The nature of the nonionic surfactants do not assume a critical character within the context of the embodiments disclosed herein. Thus, the non-ionic surfactants may, for example, be chosen from at least one of the surfactants from the following non-limiting list including polyethoxylated, polypropoxylated and polyglycerolated fatty acids; alkylphenols; α-diols; and alcohols comprising at least one fatty chain comprising, for example, from 8 to 18 carbon atoms, it being possible for the number of ethylene oxide or propylene oxide groups to range, for example, from 2 to 50 and for the number of glycerol groups to range, for example, from 2 to 30. The non-ionic surfactants may also, for example, be chosen from at least one copolymers of ethylene oxide and of propylene oxide, condensates of ethylene oxide and of propylene oxide with fatty alcohols; polyethoxylated fatty amides, for example, comprising from 2 to 30 mol of ethylene oxide, polyglycerolated fatty amides comprising on average from 1 to 5 glycerol groups, and, for example, comprising from 1.5 to 4 glycerol groups; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides and N-acylaminopropylmorpholine oxides. It will be noted that the alkylpolyglycosides constitute nonionic surfactants that can, for example, be used in the compositions disclosed herein.

(iii) Amphoteric Surfactant(s):

The amphoteric surfactants, the nature of which does not assume a critical character within the context of the embodiments disclosed herein, may be chosen, for example, from at least one of the surfactants on the following non-limiting list including, aliphatic secondary and tertiary amine derivatives wherein the aliphatic radical is chosen from linear and branched chains comprising from 8 to 22 carbon atoms and comprising at least one water-soluble anionic group (for example, the at least one water-soluble anionic group may be chosen from carboxylate, sulphonate, sulphate, phosphate and phosphonate groups); the amphoteric surfactants may also be chosen from at least one of ($C_8$–$C_{20}$)alkylbetaines, sulphobetaines, ($C_8$–$C_{20}$)alkylamido($C_1$–$C_6$)alkylbetaines and ($C_8$–$C_{20}$)alkylamido($C_1$–$C_6$)alkylsulphobetaines.

For example, among the amine derivatives, the products sold under the name Miranol, as described in U.S. Pat. Nos. 2,528,378 and 2,781,354 and with the formulae (2) and (3) may be used in the compositions disclosed herein:

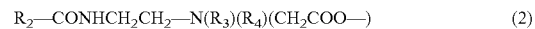

$$R_2\text{—CONHCH}_2\text{CH}_2\text{—N}(R_3)(R_4)(\text{CH}_2\text{COO—}) \qquad (2)$$

wherein $R_2$ is chosen from linear and branched $C_5$–$C_{20}$ alkyl radicals derived from an acid $R_2$—COOH present in hydrolyzed coconut oil, heptyl, nonyl and undecyl radicals, $R_3$ is a β-hydroxyethyl group and $R_4$ is a carboxymethyl group;

and

$$R_5\text{—CONHCH}_2\text{CH}_2\text{—N(B)(A)} \qquad (3)$$

wherein:

B is a —$CH_2CH_2OX'$, A is a —$(CH_2)_z$—Y', wherein z=1 or 2,

X' is chosen from a —$CH_2CH_2$—COOH group and a hydrogen atom,

Y' is chosen from a —COOH radical, a —$CH_2$—CHOH- radical, and a $SO_3H$ radical, and $R_5$ is chosen from linear and branched, saturated and unsaturated $C_5$–$C_{20}$ alkyl radicals of an acid $R_5$—COOH present in coconut oil and in hydrolyzed linseed oil; alkyl radicals, such as a $C_7$, $C_9$, $C_{11}$ and $C_{13}$ alkyl radical; a $C_{17}$ alkyl radical and the iso form thereof; and an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

For example, cocoamphodiacetate sold under the trade name Miranol C2M Concentrate by the company Rhodia Chimie may be used in the compositions disclosed herien.

(iv) Cationic Surfactant(s):

The cationic surfactants may, for example, be chosen from at least one of the following:

A) the quaternary ammonium salts of general formula (XII) below:

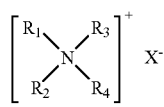

(XII)

wherein $X^-$ is an anion chosen from halides (chloride, bromide and iodide), $(C_2-C_6)$alkyl sulphates, for example, methyl sulphate, phosphates, alkyl and alkylaryl sulphonates, and anions derived from organic acid, such as acetate and lactate, and i) the radicals $R_1$ to $R_3$, which may be identical or different, are each chosen from linear and branched aliphatic radicals comprising from 1 to 4 carbon atoms, and aromatic radicals such as an aryl radical and a alkylaryl radical. The aliphatic radicals can comprise at least one hetero atom such as, at least one hetero atom chosen from oxygen, nitrogen, sulphur and halogen atoms. The aliphatic radicals may, for example, be chosen from alkyl, alkoxy and alkylamide radicals; and $R_4$ is chosen from linear and branched alkyl radicals comprising from 16 to 30 carbon atoms.

The cationic surfactants may, for example, be behenyltrimethylammonium salts (for example chloride).

ii) the radicals $R_1$ and $R_2$, which may be identical or different, are each chosen from linear and branched aliphatic radicals comprising from 1 to 4 carbon atoms and aromatic radicals such as an aryl radical and a alkylaryl radical. The aliphatic radicals can, for example, comprise at least one hetero atom, for example, at least one hetero atom chosen from oxygen, nitrogen, sulphur and halogen atoms. The aliphatic radicals may, for example, be chosen from alkyl, alkoxy, alkylamide and hydroxyalkyl radicals comprising from 1 to 4 carbon atoms;

$R_3$ and $R_4$, which may be identical or different, are each chosen from linear and branched alkyl radicals comprising from 12 to 30 carbon atoms, the radicals comprising at least one functional group chosen from ester and amide functional groups.

$R_3$ and $R_4$, may, for example, be chosen from $(C_{12}-C_{22})$alkylamido$(C_2-C_6)$alkyl and $(C_{12}-C_{22})$alkylacetate radicals.

The cationic surfactants may, for example, be stearamidopropyldimethyl(myristyl acetate)ammonium salts (for example, chloride);

B) -quaternary ammonium salts of imidazolinium, such as, that of formula (XIII) below:

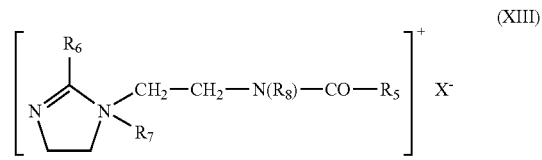

(XIII)

wherein $R_5$ is chosen from alkenyl and alkyl radicals comprising from 8 to 30 carbon atoms, for example fatty acid derivatives of tallow; $R_6$ is chosen from a hydrogen atom, $C_1-C_4$ alkyl radicals and alkenyl and alkyl radical comprising from 8 to 30 carbon atoms; $R_7$ is chosen from $C_1-C_4$ alkyl radicals; $R_8$ is chosen from a hydrogen atom and $C_1-C_4$ alkyl radicals; and X is an anion chosen from halides, phosphates, acetates, lactates, alkyl sulphates, alkyl sulphonates and alkylaryl sulphonates. $R_5$ and $R_6$, which may be identical or different, may each be chosen from mixtures of alkenyl and alkyl radicals comprising from 12 to 21 carbon atoms, such as, fatty acid derivatives of tallow, $R_7$ may be a methyl radical and $R_8$ may be a hydrogen atom. Such a product is, for example, Quaternium-27 (CTFA 1997) or Quaternium-83 (CTFA 1997), which are sold under the names REWOQUAT W75, W90, W75PG and W75HPG by the company Witco, C) -the diquaternary ammonium salts of formula (XIV):

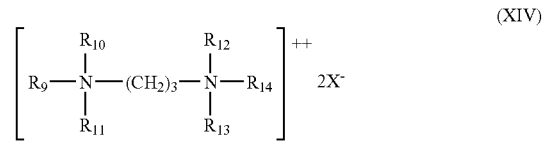

(XIV)

wherein $R_9$ is chosen from aliphatic radicals comprising from 16 to 30 carbon atoms, $R_{10}$, $R_{11}$, $R_{12}$, $R_{13}$ and $R_{14}$, which may be identical or different, are each chosen from hydrogen and alkyl radicals comprising from 1 to 4 carbon atoms, and X is an anion chosen from halides, acetates, phosphates, nitrates and methyl sulphates. Such diquaternary ammonium salts, for example, comprise propanetallowdiammonium dichloride;

D) -the quaternary ammonium salts comprising at least one ester functional group, of formula (XV) below:

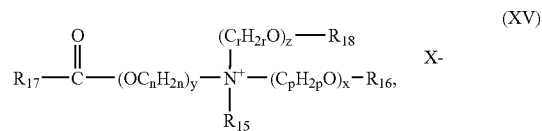

(XV)

wherein:

$R_{15}$ is chosen from $C_1-C_6$ alkyl radicals and $C_1-C_6$ hydroxyalkyl and dihydroxyalkyl radicals;

$R_{16}$ is chosen from:
a radical

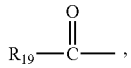

linear and branched, saturated and unsaturated $C_1$–$C_{22}$ hydrocarbon-based radicals $R_{20}$, and
a hydrogen atom;
$R_{18}$ is chosen from:
a radical

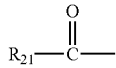

linear and branched, saturated and unsaturated $C_1$–$C_6$ hydrocarbon-based radicals $R_{22}$, and
a hydrogen atom;
$R_{17}$, $R_{19}$ and $R_{21}$, which may be identical or different, are each chosen from linear and branched, saturated and unsaturated $C_7$–$C_{21}$, hydrocarbon-based radicals;
n, p and r, which may be identical or different, are each integers ranging from 2 to 6;
y is an integer ranging from 1 to 10;
x and z, which may be identical or different, are each integers ranging from 0 to 10; and
$X^-$ is chosen from simple and complex, organic and inorganic anions; with the proviso that the sum x+y+z ranges from 1 to 15, and that when x is 0, then $R_{16}$ is $R_{20}$ and that when z is 0, then $R_{18}$ is $R_{22}$.

For example, the ammonium salts of formula (XV) may be used wherein:
$R_{15}$ is chosen from a methyl and ethyl radical,
x and y are equal to 1;
z is equal to 0 or 1;
n, p and r are equal to 2;
$R_{16}$ is chosen from:
a radical

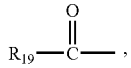

methyl, ethyl and $C_{14}$–$C_{22}$ hydrocarbon-based radicals, and
a hydrogen atom;
$R_{17}$, $R_{19}$ and $R_{21}$, which may be identical or different, are each chosen from linear and branched, saturated and unsaturated $C_7$–$C_{21}$ hydrocarbon-based radicals; and
$R_{18}$ is chosen from:
a radical

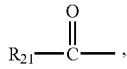

and
a hydrogen atom.

Such compounds are sold, for example, under the names DEHYQUART by the company Cognis, STEPANQUAT by the company Stepan, NOXAMIUM by the company Ceca, and REWOQUAT WE 18 by the company Rewo-Witco.

The quaternary ammonium salts may, for example, be chosen from at least one of behenyltrimethylammonium chloride and stearamidopropyldimethyl(myristyl acetate) ammonium chloride, sold under the name CERAPHYL 70 by the company Van Dyk, and QUATERNIUM-27 or QUATERNIUM-83 sold by the company Witco.

For example, anionic surfactants chosen from at least one of sodium, triethanolamine and ammonium ($C_{12}$–$C_{14}$)alkyl sulphates; sodium, triethanolamine and ammonium ($C_{12}$–$C_{14}$)alkyl ether sulphates oxyethylenated with 2.2 mol of ethylene oxide, sodium cocoyl isethionate and sodium α-($C_{14}$–$C_{16}$)olefin sulphonate, can be used, with:
  either an amphoteric surfactant such as the amine derivatives known as disodium cocoamphodipropionate or sodium cocoamphopropionate sold, for example, by the company Rhodia Chimie under the trade name MIRANOL C2M CONC as an aqueous solution containing 38% active material, or under the name MIRANOL C32;
  or an amphoteric surfactant such as alkylbetaines, for example, cocobetaine sold under the name DEHYTON AB 30 as an aqueous solution containing 32% AM by the company Cognis, or ($C_8$–$C_{20}$)alkylamido($C_1$–$C_6$) alkylbetaines, for example, TEGOBETAINE F50 sold by the company Goldschmidt.

The alkanols, may, for example, be chosen from linear and branched $C_1$–$C_4$ alkanols and, for example, ethanol and isopropanol.

The polyols may, for example, have a molecular mass of less than 1000. The polyols may, for example, be linear or branched and may comprise from 2 to 10 hydroxyl functional groups. Examples of these polyols include propylene glycol, glycerol, hexylene glycol, neopentyl glycol, isoprene glycol, 1,4-butanediol, 2-methyl-1,3-propanediol and polyethylene glycols.

The at least one adjuvant may for example, be present in an amount ranging from approximately 0.01% to approximately 20% by weight, relative to the total weight of the composition.

The dye compositions disclosed herein may further comprise at least one additional direct dye, other than the at least one direct tricationic dye of formula (I), which may, for example, be chosen from neutral, acidic and cationic nitrobenzene direct dyes; neutral, acidic and cationic azo direct dyes; neutral, acidic and cationic quinones and, for example, anthraquinone direct dyes, azine direct dyes, methine direct dyes, triarylmethane direct dyes, indoamine direct dyes and natural direct dyes.

The benzenic direct dyes may, for example, be chosen from the following compounds:
1,4-diamino-2-nitrobenzene;
1-amino-2-nitro-4-(β-hydroxyethylamino)benzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl) aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-nitrobenzene;

1-amino-2-[tris(hydroxymethyl)methylamino]-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-[bis(β-hydroxyethyl)amino]-3-nitrobenzene;
1-β-hydroxyethylamino-2-nitrobenzene; and
1-hydroxy-4-β-hydroxyethylamino-3-nitrobenzene.

The azo direct dyes may, for example, be chosen from the cationic azo dyes described in Patent Application Nos. WO 95/15144, WO 95/01772, EP 714 954, and WO 01/66646, the content of which forms an integral part of this disclosure.

Further, for example, the azo dyes may be chosen from the following dyes:
1,3-dimethyl-2-[[4-(dimethylamino)phenyl]azo]-1H-imidazolium chloride;
1,3-dimethyl-2-[(4-aminophenyl)azo]-1H-imidazolium chloride; and
1-methyl-4-[(methylphenylhydrazono)methyl]pyridinium methyl sulphate. Further examples of azo direct dyes include the following dyes described in the Colour Index International 3rd edition:
Disperse Red 17;
Acid Yellow 9;
Acid Black 1;
Basic Red 22;
Basic Red 76;
Basic Yellow 57;
Basic Brown 16;
Acid Yellow 36;
Acid Orange 7;
Acid Red 33;
Acid Red 35;
Basic Brown 17;
Acid Yellow 23;
Acid Orange 24; and
Disperse Black 9.

Further, for example, the azo direct dyes may be chosen from 1-(4'-aminodiphenylazo)-2-methyl-4-[bis(β-hydroxyethyl)amino]benzene and 4-hydroxy-3-(2-methoxyphenylazo)-1-naphthalenesulphonic acid.

The quinone direct dyes may be chosen, for example, from the following dyes:
Disperse Red 15;
Solvent Violet 13;
Acid Violet 43;
Disperse Violet 1;
Disperse Violet 4;
Disperse Blue 1;
Disperse Violet 8;
Disperse Blue 3;
Disperse Red 11;
Acid Blue 62;
Disperse Blue 7;
Basic Blue 22;
Disperse Violet 15;
Basic Blue 99;
and also the following compounds:
1-N-methylmorpholiniumpropylamino-4-hydroxyanthraquinone;
1-aminopropylamino-4-methylaminoanthraquinone;
1-aminopropylaminoanthraquinone;
5-β-hydroxyethyl-1,4-diaminoanthraquinone;
2-aminoethylaminoanthraquinone; and
1,4-bis(β,γ-dihydroxypropylamino)anthraquinone.

The azine dyes may, for example, be chosen from the following compounds:
Basic Blue 17 and
Basic Red 2.

The triarylmethane dyes may, for example, be chosen from the following compounds:
Basic Green 1;
Acid Blue 9;
Basic Violet 3;
Basic Violet 14;
Basic Blue 7;
Acid Violet 49;
Basic Blue 26; and
Acid Blue 7.

The indoamine dyes may, for example, be chosen from the following compounds:
2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N(3'-chloro-4'-methylamino)phenylureido-6-methyl-1,4-benzoquinoneimine; and
3-[4'-N-(ethylcarbamylmethyl)amino]phenylureido-6-methyl-1,4-benzoquinoneimine.

The natural direct dyes that may be used in the disclosed compositions may be chosen, for example, from lawsone, juglone, alizarin, purpurin, carminic acid, kermesic acid, purpurogallin, protocatechaldehyde, indigo, isatin, curcumin, spinulosin and apigenidin. Extracts and decoctions comprising these natural dyes may also be used, for example, henna-based poultices or extracts.

The at least one additional direct dye may, for example, be present in an amount ranging from approximately 0.001% to approximately 20% by weight, and even further, for example, from approximately 0.005% to approximately 10% by weight, relative to the total weight of the composition.

The compositions disclosed herein may further comprise at least one oxidizing agent. The at least one oxidizing agent may be chosen from any oxidizing agents conventionally used for bleaching human keratin fibres. The at least one oxidizing agent may, for example, be chosen from hydrogen peroxide, urea peroxide, alkali metal bromates, persalts such as perborates and persulphates, peracids and enzymes, such as peroxidases, 2-electron oxidoreductases such as uricases, and 4-electron oxygenases such as laccases. In one embodiment, hydrogen peroxide may be used.

When the compositions disclosed herein are intended for standard oxidation dyeing, they further comprise at least one oxidation base. The at least one oxidation base may be chosen from oxidation bases conventionally used in oxidation dyeing, for example, para-phenylenediamines, bis(phenyl)alkylenediamines, para-aminophenols, ortho-aminophenols and heterocyclic bases.

The para-phenylenediamines may, for example, be chosen from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and the acid addition salts thereof.

Further, for example, the para-phenylenediamines may be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid addition salts thereof with an acid.

The bis(phenyl)alkylenediamines may, for example, be chosen from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylamino-phenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid addition salts thereof.

The para-aminophenols may, for example, be chosen from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

The ortho-aminophenols may, for example, be chosen from 2-aminophenol, 2-amino-5-methylphenol, 2-amino-6-methylphenol and 5-acetamido-2-aminophenol, and the acid addition salts thereof.

The heterocyclic bases may, for example, be chosen from pyridine derivatives, pyrimidine derivatives and pyrazole derivatives.

For example, the pyridine derivatives that may be used are the compounds described, for example, in Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

The pyrimidine derivatives may, for example, be chosen from the compounds described in Patent Nos. DE 2 359 399; JP 88–169 571; JP 05-163 124; EP 0 770 375 or Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in Patent Application No. FR-A-2 750 048 and further examples include pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo-[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the acid addition salts thereof and the tautomeric forms thereof, when a tautomeric equilibrium exists.

The pyrazole derivatives may, for example, be chosen from compounds described in Patent Nos. DE 3 843 892 and DE 4 133 957 and Patent Application Nos. WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropyl-pyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid addition salts thereof.

The composition disclosed herein may also comprise at least one coupler conventionally used for standard oxidation dyeing of human keratin fibres. The at least one coupler may, for example, be chosen from meta-phenylenediamines, meta-aminophenols, meta-diphenols, naphthalene-based couplers and heterocyclic couplers.

Further examples of the at least one coupler include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N- methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene and the acid addition salts thereof.

In the compositions disclosed herein, the at least one coupler may be present, for example, in an amount ranging from approximately 0.001% to approximately 10% by weight, and, further, for example, from approximately 0.005% to approximately 6% by weight, relative to the total weight of the dye composition. The at least one oxidation base may be present in an amount, for example, ranging from approximately 0.001% to approximately 10% by weight approximately, and further, for example, from approximately 0.005% to approximately 6% by weight, relative to the total weight of the dye composition.

In general, the acid addition salts that may be used in the dye compositions disclosed herein for the oxidation bases and couplers may, for example, be chosen from hydrochlorides, hydrobromides, sulphates, citrates, succinates, tartrates, lactates, tosylates, benzenesulphonates, phosphates and acetates.

The medium that is cosmetically suitable for dyeing, also known as the dye support, may comprise water or a mixture of water and at least one organic solvent to dissolve the compounds that would not be sufficiently soluble in water. The at least one organic solvent may be chosen, for example, from $C_1$–$C_4$ lower alkanols, such as ethanol and isopropanol, as well as aromatic alcohols such as benzyl alcohol and phenoxyethanol.

The solvents may, for example, be present in an amount ranging from approximately 1% to approximately 40% by weight, relative to the total weight of the dye composition, and further, for example, from approximately 5% to approximately 30% by weight, relative to the total weight of the dye composition.

Needless to say, a person skilled in the art will take care to select this or these optional additional compound(s) such that the advantageous properties intrinsically associated with the dye compositions disclosed herein are not, or are not substantially, adversely affected by the addition(s) envisaged.

The pH of the dye compositions disclosed herein may, for example, range from about 3 to about 12 and, further, for example, from about 5 to about 11. It may be adjusted to the desired value using at least one agent chosen from acidifying and basifying agents usually used in the dyeing of keratin fibres, or alternatively using standard buffer systems.

Examples of acidifying agents that can be used in the compositions disclosed herein include at least one of mineral or organic acids such as hydrochloric acid, orthophosphoric acid, sulphuric acid, carboxylic acids such as acetic acid, tartaric acid, citric acid and lactic acid, and sulphonic acids.

Examples of basifying agents that can be used in the compositions disclosed herein include at least one of aqueous ammonia, alkaline carbonates, alkanolamines such as mono-, di- and triethanolamine and derivatives thereof, sodium hydroxide, potassium hydroxide and the compounds of formula (V) below:

wherein W is a propylene residue that is optionally substituted with at least one group chosen from a hydroxyl group and $C_1$–$C_4$ alkyl radicals and $R_{16}$, $R_{17}$, $R_{18}$ and $R_{19}$, which may be identical or different, are each chosen from a hydrogen atom, $C_1$–$C_4$ alkyl radicals and $C_1$–$C_4$ hydroxyalkyl radicals.

The compositions disclosed herein may further comprise at least one additional additive, for example, chosen from antioxidants, penetration agents, sequestering agents, fragrances, dispersing agents, packaging agents such as silicones, which may or may not be volatile and modified, fatty substances including ceramides and fatty alcohols, preserving agents, opacifiers, and anionic and cationic polymers.

The dye compositions disclosed herein may be provided in various forms, such as, liquids, creams and gels, and any other forms that are suitable for dyeing human keratin fibres, such as human hair.

Further disclosed herein is a process for direct dyeing, comprising applying at least one dye composition comprising at least one direct tricationic dye of formula (I) as defined above to human keratin fibres. After a leave-in time, the fibres are rinsed, revealing colored fibres.

The at least one dye composition comprising the at least one direct tricationic dye of formula (I) may be applied to the fibres in the presence of at least one oxidizing agent, which causes bleaching of the fibres (lightening direct dyeing). The at least one oxidizing agent may be added to the composition comprising the at least one direct tricationic dye at the time of use or directly onto the fibres.

Further disclosed herein is a process for oxidation dyeing, comprising applying to the human keratin fibres at least one dye composition comprising at least one direct tricationic dye of formula (I), at least one oxidation base and optionally at least one coupler, in the presence of at least one oxidizing agent.

The at least one oxidation base, the at least one coupler and the at least one oxidizing agent are as defined above.

The color may be revealed at acidic, neutral or alkaline pH and the at least one oxidizing agent may be added to the compositions disclosed herein at the time of use, or it may be introduced using the at least one oxidizing composition comprising it, applied to the fibres simultaneously with or sequentially to the at least one dye composition.

In the case of oxidation dyeing or lightening direct dyeing, the at least one dye composition is mixed, for example, at the time of use, with at least one oxidizing composition comprising, in a medium that is suitable for dyeing, at least one oxidizing agent, wherein the at least one oxidizing agent is present in an amount that is sufficient to develop a coloration. The mixture obtained is then applied to the fibres. After a leave-in time of approximately 3 to approximately 50 minutes, for example, from approximately 5 to approximately 30 minutes, the fibres are rinsed, washed with shampoo, rinsed again and then dried.

The at least one oxidizing composition may further comprise various adjuvants conventionally used in compositions for dyeing the hair, and as defined above.

The pH of the at least one oxidizing composition comprising the at least one oxidizing agent is such that, after mixing with the at least one dye composition, the pH of the resulting composition applied to the keratin fibres, for example, ranges from about 3 to about 12, and even further, for example, from about 5 to about 11. It may be adjusted to the desired value by means of at least one agent chosen from acidifying and basifying agents usually used in the dyeing of human keratin fibres, and as defined above.

The composition that is finally applied to the fibres may be in various forms, such as in a form chosen from liquids, creams and gels and any other forms that are suitable for dyeing human keratin fibres, such as hair.

Further disclosed herein is a multi-compartment device or dyeing "kit", for example, a 2-compartment device, wherein a first compartment comprises the at least one dye composition disclosed herein and a second compartment comprises the at least one oxidizing composition. This device may be equipped with a means for applying the desired mixture to the hair, such as the devices described in Patent No. FR-2 586 913.

The examples that follow, of dye compositions, are intended to illustrate the embodiments disclosed herein without being limiting in nature.

EXAMPLE 1

The dye composition below was prepared:

| | |
|---|---|
| Bis [2-({4-[(4-dimethylaminophenyl)(cyclohexa-2,5-dienylidene}-4-dimethylammonium)methylene]phenyl}-ethylamino)ethyl]dimethylammonium trichloride | 0.95 g |
| Benzyl alcohol | 4.0 g |
| Polyethylene glycol 6 EO | 6.0 g |
| Hydroxyethylcellulose | 0.7 g |
| Alkylpolyglucoside as an aqueous solution containing 60% A.M.* | 4.5 g A.M. |
| Phosphate buffer q. s | pH 7 |
| Demineralized water q. s | 100 g |

*Active Material

The above composition was applied to locks of natural or permanent-waved grey hair containing 90% white hairs, and was left on the hair for 20 minutes. After rinsing with running water and drying, the hair was dyed in a violet shade.

EXAMPLE 2

The dye composition below was prepared:

| | |
|---|---|
| Benzothiazolium 2,2'-[(methylpropylimino)bis[(2-hydroxytrimethylene)(ethylimino)-p-pheylenazo]]bis[6-ethoxy-3-methyl trichloride, diacetate ester | 1.06 g |
| Oleic acid diethanolamide | 3 g |
| Lauric acid | 1 g |
| Ethylene glycol monoethyl ether | 5 g |
| Hydroxyethylcellulose | 2 g |
| 2-Amino-2-methyl-1-propanol q.s | pH 9.5 |
| Demineralized water q.s | 100 g |

The above composition was applied to locks of natural or permanent-waved grey hair containing 90% white hairs, and was left on the hair for 30 minutes. After rinsing with running water and drying, the hair was dyed in a blue shade.

What is claimed is:

1. A dye composition for dyeing human keratinous fibres, comprising, in a medium suitable for dyeing, at least one direct tricationic dye of formula (I) below:

$$Col\!-\!Z\!-\!Col \qquad (I)$$

wherein:
Col, which may be identical or different, is a monocationic dye chosen from azo dyes, methine dyes, azomethine dyes, phenothiazine dyes, triarylmethane dyes, xanthene dyes, phenanthridine dyes and phthalocyanin dyes and Z is chosen from linear and branched, saturated and unsaturated $C_1$–$C_{20}$ hydrocarbon-based groups comprising at least one nitrogen atom and bearing a cationic charge.

2. The composition according to claim 1, wherein the keratinous fibers are hair.

3. The composition according to claim 1, wherein Z is chosen from aliphatic groups of formula (II):

wherein:
n is an integer ranging from 1 to 10;
p is an integer ranging from 1 to 10; and
$Z_4$ is chosen from a radical $^+NR_1R_2$, wherein $R_1$ and $R_2$, which may be identical or different, are each chosen from $C_1$–$C_6$ alkyl radicals; and a 5- to 8-membered monocationic heterocycle, which may or may not be fused to a benzene nucleus and which is optionally substituted with at least one entity chosen from halogen atoms and $C_1$–$C_4$ alkyl, hydroxyl and amino radicals.

4. The composition according to claim 3, wherein n is an integer ranging from 2 to 5.

5. The composition according to claim 3, wherein p is an integer ranging from 2 to 5.

6. The composition according to claim 3, wherein $Z_4$ is a $^+NR_1R_2$ radical.

7. The composition according to claim 3, wherein the Col group is chosen from at least one of triarylmethane dyes, azo dyes, and azomethine dyes.

8. The composition according to claim 1, wherein the at least one direct tricationic dye of formula (I) is chosen from:
1-Hexadecanaminium 16,16'-[(dimethylimino)bis(16,1-hexadecanediyloxy-4,1-phenylenemethylidynenitrilo-4,1-phenyleneoxy)]bis[N,N,N-trimethyl tribromide;
1-Decanaminium 10,10'-[(dimethylimino)bis(10,1-decanediyloxy-4,1-phenylenemethylidynenitrilo-4,1-phenyleneoxy)]bis[N,N,N-trimethyl tribromide;
bis[2-({4-[(4-Dimethylaminophenyl)(cyclohexa-2,5-dienylidene}-4-dimethylammonium)methylene]phenyl}ethylamino)ethyl]dimethyl ammonium
bis[2-({4-[(4-Dimethylaminophenyl)(cyclohexa-2,5-dienylidene}-4-dimethylammonium)methylene]phenyl}ethylamino)ethyl]ethylmethyl ammonium; and
benzothiazolium 2,2'-[(methylpropylimino)bis-[(2-hydroxytrimethylene)(ethylimino)-p-phenyleneazo]]bis [6-ethoxy-3-methyl trichloride, diacetate ester.

9. The composition according to claim 1, wherein the at least one direct tricationic dye of formula (I) is present in an amount ranging from approximately 0.001% to approximately 5% by weight, relative to the total weight of the dye composition.

10. The composition according to claim 9, wherein the at least one direct tricationic dye of formula (I) is present in an amount ranging from approximately 0.05% to approximately 2% by weight, relative to the total weight of the dye composition.

11. The composition according to claim 1, further comprising at least one cosmetic adjuvant chosen from monoalcohols; polyols; anionic, cationic, nonionic, amphoteric and zwitterionic surfactants; mineral and organic thickeners; and anionic, cationic, nonionic and amphoteric associative polymers.

12. The composition according to claim 1, further comprising at least one additional direct dye, other than the at least one direct tricationic dye of formula (I), chosen from neutral, acidic and cationic nitrobenzene direct dyes; neutral, acidic and cationic azo direct dyes; neutral, acidic and cationic quinone dyes; azine direct dyes; methine direct dyes; triarylmethane direct dyes; indoamine direct dyes; and natural direct dyes.

13. The composition according to claim 12, wherein the neutral, acidic and cationic quinone dyes are anthraquinone direct dyes.

14. The composition according to claim 1, further comprising at least one oxidizing agent.

15. The composition according to claim 14, wherein the at least one oxidizing agent is hydrogen peroxide.

16. The composition according to claim 1, further comprising at least one oxidation base.

17. The composition according to claim 16, wherein the at least one oxidation base is chosen from para-phenylenediamines, bis(phenyl)alkylenediamines, para-aminophenols, ortho-aminophenols and heterocyclic bases, and the acid addition salts thereof.

18. The composition according to claim 16, further comprising at least one coupler.

19. The composition according to claim 18, wherein the at least one coupler is chosen from meta-phenylenediamines, meta-aminophenols, meta-diphenols, naphthalene-based couplers and heterocyclic couplers, and the acid addition salts thereof.

20. A process for direct dyeing of human keratin fibres, comprising applying to the fibres at least one dye composition comprising, in a medium suitable for dyeing, at least one direct tricationic dye of formula (I) below:

$$\text{Col-Z-Col} \quad \text{(I)}$$

wherein:
Col, which may be identical or different, is a monocationic dye chosen from azo dyes, methine dyes, azomethine dyes, phenothiazine dyes, triarylmethane dyes, phenanthridine dyes and phthalocyanin dyes and Z is chosen from linear and branched, saturated and unsaturated $C_1$–$C_{20}$ hydrocarbon-based groups comprising at least one nitrogen atom and bearing a cationic charge.

21. The process according to claim 20, wherein the human keratin fibers are hair.

22. The process according to claim 20, wherein the at least one dye composition further comprises at least one oxidizing agent.

23. The process according to claim 22, comprising, mixing, at the time of use, the at least one oxidizing agent and the at least one dye composition.

24. The process according to claim 22, wherein the at least one oxidizing agent is applied to the keratin fibers in the form of at least one oxidizing composition, simultaneously with or sequentially to the at least one dye composition.

25. A process for the oxidation dyeing of human keratin fibres comprising applying to the keratin fibers, in the presence of at least one oxidizing agent, at least one dye composition comprising, in a medium suitable for dyeing, at least one direct tricationic dye of formula (I) below:

$$\text{Col-Z-Col} \quad \text{(I)}$$

wherein:
Col, which may be identical or different, is a monocationic dye chosen from azo dyes, methine dyes, azomethine dyes, phenothiazine dyes, triarylmethane dyes, phenanthridine dyes and phthalocyanin dyes, and Z is chosen from linear and branched, saturated and unsaturated $C_1$–$C_{20}$ hydrocarbon-based groups comprising at least one nitrogen atom and bearing a cationic charge;

at least one oxidation base; and optionally, at least one coupler.

26. The process according to claim 25, wherein the human keratin fibers are hair.

27. The process according to claim 25, comprising, mixing, at the time of use, the at least one oxidizing agent comprising the oxidizing agent and the at least one dye composition.

28. The process according to claim 25, wherein the at least one oxidizing agent is applied to the keratin fibers in the form of at least one oxidizing composition, simultaneously with or sequentially to the at least one dye composition.

29. A multi-compartment device or kit, for dyeing human keratin fibres, comprising a first compartment comprising, in a medium suitable for dyeing, at least one direct tricationic dye of formula (I) below:

$$\text{Col-Z-Col} \quad \text{(I)}$$

wherein:
Col, which may be identical or different, is a monocationic dye chosen from azo dyes, methine dyes, azomethine dyes, phenothiazine dyes, triarylmethane dyes, phenanthridine dyes and phthalocyanin dyes, and Z is chosen from linear and branched, saturated and unsaturated $C_1$–$C_{20}$ hydrocarbon-based groups comprising at least one nitrogen atom and bearing a cationic charge and a second compartment comprising at least one oxidizing composition.

30. The kit according to claim 29, wherein the human keratin fibers are hair.

31. A method of preparing a composition for direct dyeing human keratin fibers comprising including in the composition at least one direct tricationic dye of formula (I) below:

$$\text{Col-Z-Col} \quad \text{(I)}$$

wherein:
Col, which may be identical or different, is a monocationic dye chosen from azo dyes, methine dyes, azomethine dyes, phenothiazine dyes, triarylmethane dyes, phenanthridine dyes and phthalocyanin dyes, and Z is chosen from linear and branched, saturated and unsaturated $C_1$–$C_{20}$ hydrocarbon-based groups comprising at least one nitrogen atom and bearing a cationic charge.

32. The method according to claim 31, wherein the human keratin fibers are hair.

* * * * *